(12) United States Patent
Nadal

(10) Patent No.: US 6,527,962 B1
(45) Date of Patent: Mar. 4, 2003

(54) BLOOD FILTER HAVING LEGS AND CENTERING ELEMENTS INTEGRALLY MANUFACTURED

(75) Inventor: Guy Nadal, Poitiers (FR)

(73) Assignee: B. Braun Medical (FR)

( * ) Notice: Subject to any disclaimer, the term of this patent is extended or adjusted under 35 U.S.C. 154(b) by 289 days.

(21) Appl. No.: 09/717,556

(22) Filed: Nov. 21, 2000

(30) Foreign Application Priority Data

Nov. 26, 1999 (FR) .............................................. 99 14900

(51) Int. Cl.[7] .................................................. A61F 3/00
(52) U.S. Cl. ......................... 216/8; 623/1.11; 623/1.12; 623/901; 604/190; 606/200
(58) Field of Search ........................ 604/103.02, 96.01, 604/525, 526, 190, 200; 606/1, 27, 200, 41, 28; 623/1.11, 1.12, 901; 422/44–48; 216/8, 92

(56) References Cited

U.S. PATENT DOCUMENTS

| | | |
|---|---|---|
| 4,688,553 A | 8/1987 | Metals |
| 5,108,418 A | 4/1992 | Lefebvre |
| 5,344,427 A | 9/1994 | Cottenceau et al. |
| 5,383,887 A | 1/1995 | Nadal |
| 5,421,955 A | 6/1995 | Lau et al. |
| 5,634,942 A * | 6/1997 | Chevillon et al. ........... 623/1.1 |
| 6,436,120 B1 * | 8/2002 | Meglin ....................... 606/200 |

FOREIGN PATENT DOCUMENTS

| | | |
|---|---|---|
| EP | 0 759 287 A1 | 2/1997 |
| EP | 0 709 067 A3 | 6/1997 |
| EP | 0 714 641 B1 | 6/1999 |
| FR | 2 570 288 A1 | 3/1986 |
| FR | 2 764 503 B1 | 10/1999 |
| WO | WO 99 23976 | 5/1999 |
| WO | WO 99 25252 | 5/1999 |

* cited by examiner

*Primary Examiner*—Allan Olsen
(74) *Attorney, Agent, or Firm*—Skinner and Associates

(57) ABSTRACT

The method for manufacturing a blood filter adapted to be disposed in a blood vessel comprises, in the invention, the steps of a) providing a thin wall comprising a biocompatible material, b) producing in said thin wall a series of essentially parallel elongated sections, for defining the elongated legs, and having the elongated legs joined to each other, at a first end of the elongated sections, wherein step b) comprises the steps of producing adjacent essentially parallel strips comprising a first strip and a second strip separated by a slot, the strips extending essentially parallel the axis and each slot being interrupted at a distance from a second end of the elongated sections, so that the first and the second strips are connected to each other at said second end, by a continuous zone of said thin wall, and having the first strip of the elongated sections joined to each other, at said first end thereof.

6 Claims, 3 Drawing Sheets

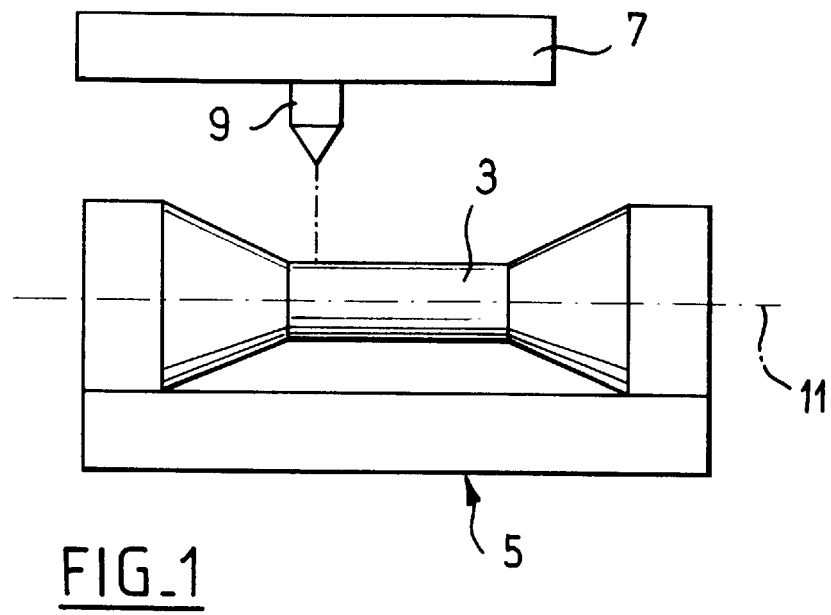
FIG_1
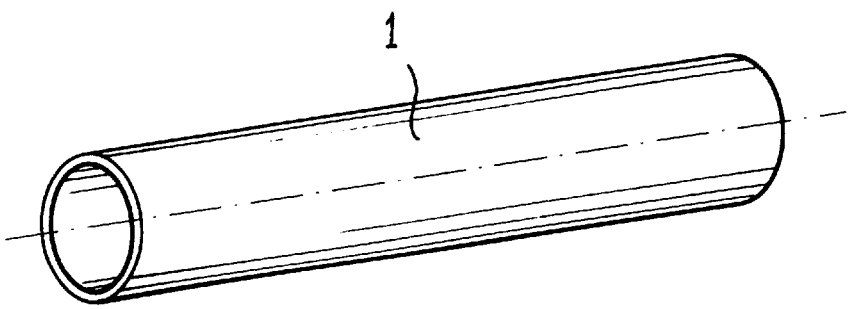
FIG_2
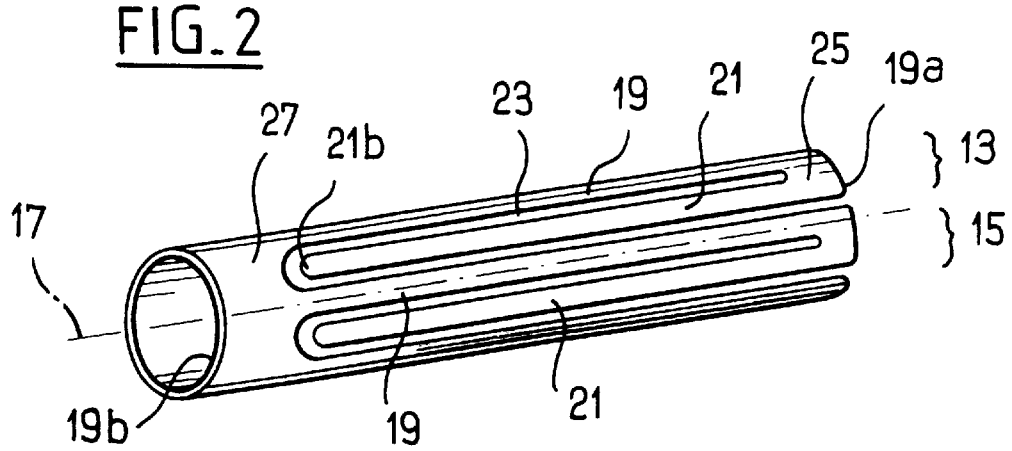
FIG_3

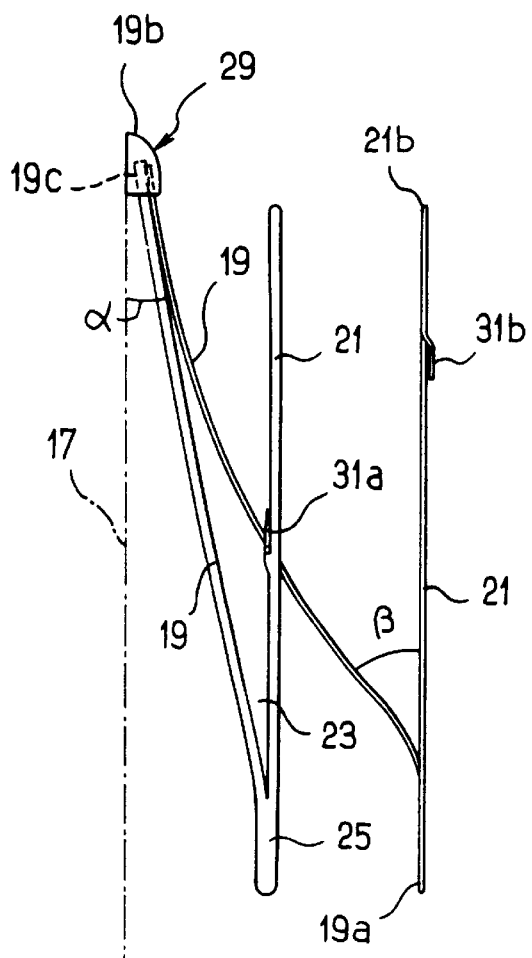
FIG_4
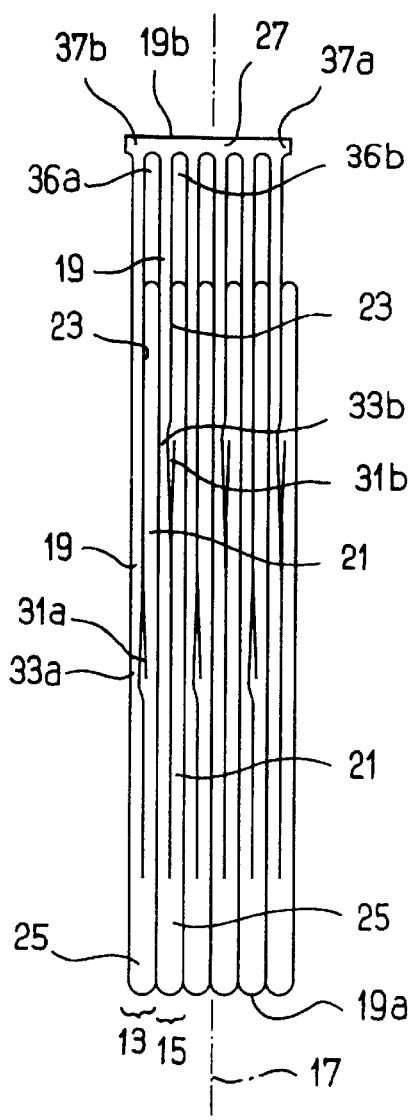
FIG_5
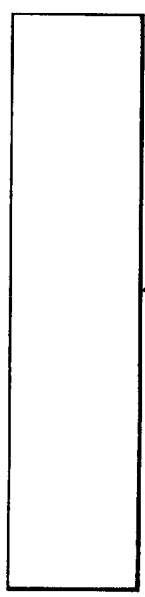
FIG_6

BLOOD FILTER HAVING LEGS AND CENTERING ELEMENTS INTEGRALLY MANUFACTURED

BACKGROUND OF THE INVENTION

The invention relates to a process for manufacturing a blood filter adapted to be disposed within a blood vessel of a mammal body. A specific blood filter is also concerned.

Blood filters are already known.

For manufacturing blood filters, elongated legs are typically created, together with at least a head for joining the legs together, locally. The legs typically extend round an axis of the filter and are radially movable with respect to the axis and the head, between a first, radially restricted position and a second, radially expanded position in which the legs are diverging from the axis (located farer therefrom than in the first position, along a portion of their length).

Examples of such blood filters can be found in U.S. Pat. No. 4,688,553 or U.S. Pat. No. 5,344,427.

So, the prior art discloses the following steps for manufacturing a blood filter:

(a) using a wall comprising a biocompatible material, and
(b) for defining the legs of the blood filter, creating through said wall a series of elongated, essentially parallel sections having a first free end and a second opposed end.

BRIEF SUMMARY OF THE INVENTION

An object of the invention is to improve the steps of manufacturing blood filter.

The following objects are especially expected:

reducing the steps of assembling the different portions of the filter (legs, head . . . ), reducing the risks possibly induced by local, mechanical constraints created during the steps of manufacturing the blood filter, improving the cohesion between the above-mentioned different portions of the filter, potentially reducing the costs for manufacturing the filter, using possible synergies between the blood filters and the stents or stent grafts.

To that aim, an important feature of the invention recommends to make use of the following steps of manufacturing:

(c) in at least some of the wall sections materialized during the above-mentioned step (b), adjacent, essentially parallel strips (having a non circular transversal section) are created, said strips comprising at least a first strip and a second strip separated by a slot, the strips extending essentially parallel the axis and the slots interrupting at a distance from the first free end of the corresponding wall sections, so that the first strips are integral with the second strips at said first free end, while the second strips are freely movable from the first strips all along the slots (and especially at the second end of the wall sections), (d) and the first strips are connected therebetween, at the second end.

Even if reducing the mechanical constraints within the blood filter as manufactured is an important object, the invention preferably recommends a further step of angularly shifting the second strips with respect to the first strips, so that in the second position, the first strips are angulated with respect to the axis of the blood filter, while the second strips extend substantially parallel the axis.

It is to be noted that such an <<angular shifting>> is typically comprised between 30° and 40°, what induces less mechanical constraints in the blood filter than folding back sections of a metallic wire for forming an air pin, as disclosed in U.S. Pat. Nos. 4,688,553, 5,344,427 or 5,383,887.

Further, welding a wire and a metallic plate as in FR-A-2 764 503 is avoided.

For angularly shifting the corresponding strips, the strips can be mechanically moved or a thermal treatment together with a shape-memory material, such as a super-elastic metallic alloy (NiTi) can be used for shifting said strips and for having the first strips moved between the first and second positions.

For improving the reliability of the filter while limiting the costs of manufacturing, it is further recommended, during the step (a), to use an essentially tubular wall and, during step (b), to connect all the first strips one to the others by using a connecting element to which every first strip is fixed, at said second end, the first strips being regularly disposed round the axis.

With reference to the blood filter, the following distinctive features are to be noted: the wall sections <<cut>> in the original wall individually have the shape of a plate (showing a non circular section) and comprise at least two strips separated by a slot which is interrupted at a distance from the first end, so that the first strips are integral with the second strips at said first end, so that said firststrips define the legs of the blood filter and the second strips define centering elements for centering the blood filter within the blood vessel.

DESCRIPTION OF THE FIGURES

FIG. 1 diagrammatically shows a laser cutting machine adapted for cutting the tube shown on FIG. 2 (enlarged view), FIG. 3 diagrammatically shows the tube of FIG. 2 after the cutting process, FIG. 4 shows a partial view of a filter manufactured according to the invention, the filter being in its radially expanded position (enlarged view), FIG. 5 shows a way for obtaining a blood filter according to the invention from a flat plate such as illustrated on FIG. 6, FIGS. 7 and 8 diagrammatically show two solutions for maintaining the head of the filter in a curved position round the axis of said filter, FIGS. 9, 10 and 11 diagrammatically show three embodiments of the legs and centering elements of the blood filter, FIG. 12 diagrammatically shows how to cut the shape illustrated on FIG. 9, from a thin tubular wall.

DETAILED DESCRIPTION OF PREFERRED EMBODIMENTS

Figure 7:
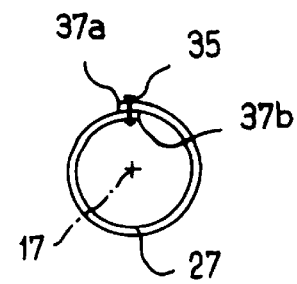

On FIG. 1, a laser cutting machine is shown. Such a machine can be used for manufacturing a blood filter from a continuous, solid wall having the shape of a tube.

Laser cutting is already disclosed in EP-B-0 714 641 (column 9, line 24-column 10, line 9): a thin, essentially tubular wall having a small diameter (such as a cylindrical, metallic tube having a constant section, as referenced 1 on FIG. 2) is disposed round a rotatable mandrel 3 of a numerally driven machine 5 provided with a shaft 7 having a laser 9, such as a Nd laser. Tube 1 is disposed round the mandrel 3, then rotated and longitudinally moved (along the axis 11) with respect to the laser beam. Portions of the tube material are selectively removed by the laser beam, according to the required shape which presently corresponds to the diagrammatical illustration of FIG. 3.

Cutting the wall can be operated by using another process: for example, the wall can be <<cut>> by chemical etching or by a hot knife, or even by using a $CO_2$ laser (see U.S. Pat. No. 5,421,955, column 6, line 31-column 7, line 32). A chemical etching process is disclosed in EP-A-0 709 067 (column 2, line 38-column 3, line 28).

On FIG. 3, the blood filter comprises elongated, essentially parallel sections of wall, such as referenced 13 and 15. The elongated sections are essentially parallel the longitudinal axis 17 of the filter (which corresponds to the axis 11 of the tube).

Angularly, the elongated sections 13, 15 are regularly disposed round the axis.

Therefore, what is true in the present description with reference to a specific elongated section (such as referenced 13) is also true for the other elongated sections. The elongated section 13 comprises two strips of wall 19, 21, separated by a slot 23 essentially parallel the axis 17. Slot 23 is interrupted at a distance from the free end 19a of the first strip 19, while it opens at the opposed end, 21b, so that the two strips 19, 21 are connected (or joined) only near, or at, the free end 19a (by a zone of wall 25), while said strips are free of moving one with respect to the other, along the slot 23 (and especially at the end 21b which thus defines a free end for the second strip 21).

If the proximal end of the filter, opposed to the above-mentioned <<free end>> 19a (also called distal end), is referenced 19b, it will further be noted that all the <<first strips>>, such as 19, are connected (or joined) together by a connecting means which is presently defined by a strip (or band) 27 of wall extending transversally (especially perpendicular) the axis 17 along which the wall section and strips extend. The strip 27 is integral with all the first strips (such as 19) and connects them one to the other, in the immediate vicinity of the proximal end 19b.

On FIG. 4, an illustration more in conformity with a real blood filter than the illustration of FIG. 3, is shown. However, only some of the wall sections as cut are illustrated, for sake of clarity.

It is also to be noted that on FIG. 3, the blood filter can be considered as illustrated in its <<radially restricted state>>, (viz. the state it holds within the introducing catheter), whereas on FIG. 4, the filter is in its <<radially expanded stated >>, viz. as it holds within the vessel for filtering any blood clots therein.

Especially on FIG. 4, it is shown that the first strips of the wall, such as 19, define legs which are inclined with respect to axis 17, whereas the <<second strips>> 21 define centering (or stabilizing) integrated elements.

The angulation α, in such a radially expanded state, of the legs such as 19 with respect to the axis 17, may be of about 30° to 40°. The angulation α is substantially identical to angulation β corresponding to the angulation between the legs and the centering elements (which have to be directed parallel the axis 17, along a generating line of cylinder having a constant section).

The apex of angulation α is located at the proximal end 19b of the filter (typically called <<filter head>>). The cone of filtration defined by the legs opens up to the distal end 19a where the legs are far away one from the others, in the radially expanded state of FIG. 4.

The following material (or covering) can be cited for the original wall 1: stainless steel, nitinol® which is a super elastic alloy having a thermal memory shape, titanium, or even plastic material (such as thermoplastic polymer). So, the state illustrated on FIG. 4 can be reached by the natural elasticity of the strips 19, 21, or further to a variation of temperature if a thermal memory alloy is used.

Two structural differences can be found between the illustrations of FIGS. 3 and 4: on FIG. 4, the first strips, such as 19, are connected to one another, near the end 19b, by using a complementary member 29. Further, the anchors such as 31a, 31b, are integrated to the centering elements 21.

The complementary member 29 is a metallic, partially hollow cap within which the legs are welded. With such a connection, the legs 19, before being connected one to the other by the cap 29, are independent. Those independent legs (which then have a free end 19c) are disposed in a close position at said end and are connected to the cap 29 which thus, define the connecting head of the legs.

The creation of the integrated anchors 31a, 31b is clearly illustrated on FIG. 5 which shows an embodiment (not the best mode) for manufacturing the filter illustrated on FIG. 4, from a flat plate, such as the plate referenced 30 on FIG. 6.

On FIG. 5, the flat wall 30 is already <<cut>>, viz. slots defining the strips having a plate shape (thus showing a non circular section) have been created for defining the legs and integrated centering elements of the filter.

On FIG. 5, the parallel wall sections defined by the cuts of the plate begin from the upper connecting band 27. The resulting parallel wall sections, such as those referenced 13, 15, one more time, comprise a first strip 19 having a reduced width referenced 33a, 33b, said first strip extending at the axial end 19a (opposite the band 27) by a second strip (such as 21) integral with the first strip (the hairpin connection zone between the first and second strips is referenced 25).

At the level of the reduced width 33a, 33b, the second strips have also a reduced width for defining the corresponding integrated anchors, such as 31a, 31b.

Towards the proximal end 19b, the second strips 21 are interrupted at a distance from the end, so that the second (<<backward>>) strips are shorter than the first (<<frontward>>) strips. Thus, hollow spaces, such as 36a, 36b are materialized through the wall.

After having created such a shape, the first strips 19 are angularly shifted with respect to the transversal band 27, whereas the second strips 21 are maintained substantially parallel the axis 17.

Before that step, or after, the resulting shape is rolled on itself round the axis 17.

Thus, a blood filter having elongated legs showing the shape of a substantially frustoconical shape, having an axial opening through its band 27 (head) and a free end 19a where, in such a radially expanded state, the filter shows its larger diameter, is created.

A welding 35 can be used for maintaining the filter rolled on itself, at its head zone 27, where the two opposed ends 37a, 37b of the wall can overlap, as illustrated on FIG. 7.

Figure 8:
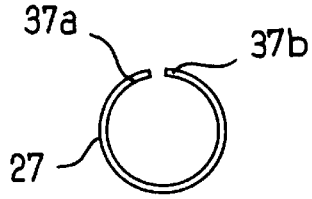

Alternatively, FIG. 8 shows that those two ends can face each other, with no fixation means therebetween.

Figure 9:
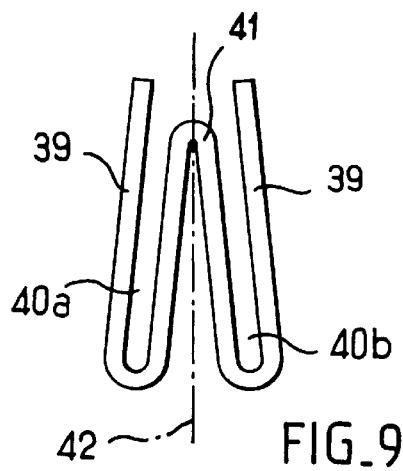
Figure 11:
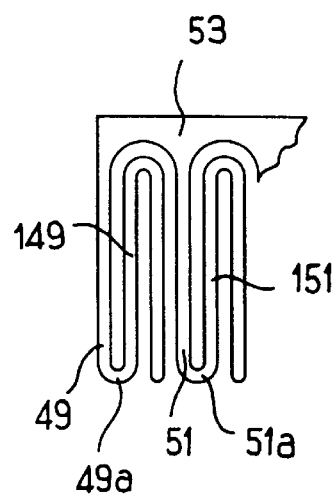
Figure 10:
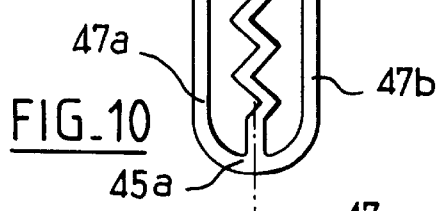

On FIGS. 9, 10 and 11, are diagrammatically illustrated some among other possible shapes for the legs and centering elements of the blood filter.

So, on FIG. 9, a <<W>> shape is shown comprising two lateral strips 39 defining the legs of the filter. Each strip 39 is integral with a central centering member 41 having the shape of an inverted <<V>>. Two slots 40*a*, 40*b* define an inverted <<V>>, so that they are essentially parallel to the axis 42.

Figure 12:
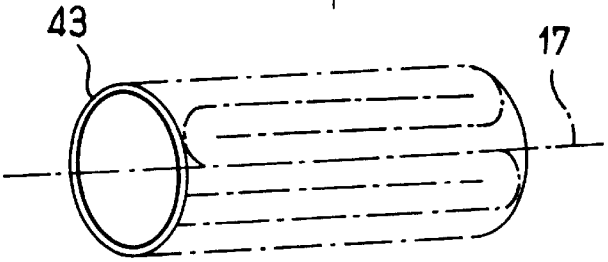

Such shapes can be created for example from the tube 43 of FIG. 12 in which strips are cut as illustrated, the strips being thereafter slightly angularly shifted for obtaining the required filter shape.

On FIG. 10 is illustrated a central elongated leg having a zigzag shape (so essentially parallel to the axis 47 of the filter). Said elongated leg 45 is integrally connected with two lateral centering members 47*a*, 47*b*, at the end 45*a*.

On FIG. 11, two legs 49, 51 are diagrammatically illustrated. Those two legs are integrally connected with a continuous, transversal band 53 and extend, at an end opposite said band (respectively referenced 49*a* and 51*a*), in centering members having an inverted <<V>> shape, respectively referenced 149 and 151.

Those examples show that various shapes can be created for the legs and the centering elements (or members) of the filter. An important feature is to draw one or a series of leg(s) and centering element(s) from an original wall in which the required shape is <<cut>> (viz. created), together with at least one slot essentially parallel the axis of the blood filter (which axis can be considered as the same than the axis of the blood vessel, once the filter is implanted in said vessel).

Figure 13:
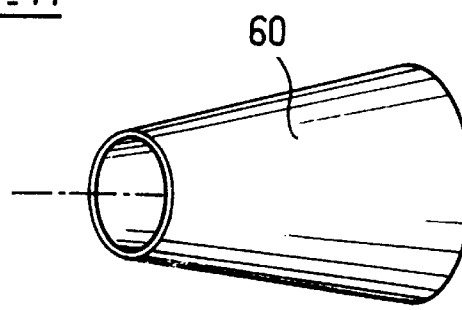
FIG. 13 shows an invaginated tubular wall.

It is further to be noted that the tubular wall of FIG. 2 could be changed to an invaginated tubular wall 60 (especially a frustoconical wall) such as the wall illustrated on FIG. 13.

I claim:

1. A method for manufacturing a blood filter adapted to be disposed in a blood vessel, the blood filter having an axis and comprising elongated legs extending around the axis, the method comprising the steps of:
    a) providing a thin wall comprising a biocompatible material,
    b) from the thin wall, producing a series of essentially parallel elongated sections, for defining the elongated legs, the elongated sections having a longitudinal first end and a longitudinal second end,
    c) joining the elongated legs to each other, at the first end of the elongated sections, so that the elongated legs are radially movable between a first position in which the legs are radially expanded and a second position in which the legs are radially restricted,
    wherein step b) comprises the step of:
    d) in at least some of said parallel elongated sections, producing adjacent essentially parallel strips comprising a first strip and a second strip separated by a slot, the strips extending essentially parallel the axis and each slot being interrupted at a distance from the second end, so that the first and the second strips are connected to each other at the second end, by a continuous zone of said thin wall,
    and wherein step c) comprises the step of:
    e) joining the first strip of the elongated sections to each other, at said first end thereof.

2. The method of claim 1, further comprising the step of:
    f) angularly shifting one with respect to the other, the respective first and second strips of the elongated sections, so that the first strips connected to each other at said first end define the elongated legs of the blood filter and are angulated with respect to the axis, in the second position, and the second strips are oriented essentially parallel the axis in said second position.

3. A method for manufacturing a blood filter adapted to be disposed in a blood vessel, the blood filter having an axis and comprising elongated legs extending around the axis, the method comprising the steps of:
    a) providing a thin wall comprising a biocompatible material and having a tubular surface,
    b) from the thin wall, producing a series of essentially parallel elongated sections, for defining the elongated legs, the elongated legs having a free end and being radially movable between a first position in which the legs are radially expanded and a second position in which they are radially restricted,
    wherein step b) further comprises the steps of:
    c) in at least some of said parallel elongated sections producing adjacent essentially parallel strips comprising a first strip and a second strip separated by a slot, the strips extending essentially parallel the axis and each slot being interrupted at a distance from the free end, so that the first and the second strips are connected to each other at said free end, by a continuous zone of the thin wall,
    d) on said thin wall, at an end opposite said free end, keeping a connecting section extending transversal the elongated sections which are thus integral with said transversal section, so that the elongated legs are joined to each other around the axis by the transversal section.

4. A method for manufacturing a blood filter adapted to be disposed in a blood vessel, the blood filter having an axis and comprising elongated legs extending around the axis, the method comprising the steps of:
    a) providing a thin wall comprising a biocompatible material, and having a non-tubular surface,
    b) producing a series of essentially parallel elongated sections from the thin wall, for defining the elongated legs, the elongated legs having a free end and being radially movable between a first position in which the legs are radially expanded and a second position in which they are radially restricted, wherein step b) further comprises the steps of:
    c) producing adjacent essentially parallel strips comprising a first strip and a second strip separated by a slot, in at least some of said parallel elongated sections, the strips extending essentially parallel the axis and each slot being interrupted at a distance from the free end, so that the first and the second strips are connected to each other at said free end, by a continuous zone of said thin wall,
    d) on the thin wall and at an end opposite said free end, keeping a connecting section extending transversal the elongated sections which are thus integral with said transversal section, so that the elongated legs are joined to each other by the transversal section, and
    e) rolling the transversal section and the parallel elongated sections around the axis.

5. The method according to claim 1, wherein the step b) comprises the step of producing the series of essentially parallel elongated sections by cutting the thin wall with a laser beam.

6. The method according to claim 1, wherein the step b) comprises the step of producing the series of essentially parallel elongated sections by chemical etching.

* * * * *